United States Patent [19]

Danziger et al.

[11] 4,239,682

[45] Dec. 16, 1980

[54] PURIFICATION OF CAPROLACTAM

[75] Inventors: Harry Danziger; Bernd-Ulrich Kaiser, both Krefeld, Fed. Rep. of Germany

[73] Assignee: Bayer Aktiengesellschaft, Leverkusen, Fed. Rep. of Germany

[21] Appl. No.: 740,416

[22] Filed: Nov. 10, 1976

[30] Foreign Application Priority Data

Nov. 13, 1975 [DE] Fed. Rep. of Germany ....... 2550934

[51] Int. Cl.$^3$ .............................................. C07D 20/16
[52] U.S. Cl. .............................................. 260/239.3 A
[58] Field of Search ................................. 260/239.3 A

[56] References Cited

U.S. PATENT DOCUMENTS

| | | | |
|---|---|---|---|
| 2,221,369 | 11/1940 | Cass | 260/239.3 A |
| 2,973,355 | 2/1961 | Bauer | 260/239.3 A |
| 3,948,888 | 4/1976 | Schwarz et al. | 260/239.3 A |

FOREIGN PATENT DOCUMENTS

| | | | |
|---|---|---|---|
| 1031808 | 6/1958 | Fed. Rep. of Germany | 260/239.3 A |
| 294693 | 2/1954 | Switzerland | 260/239.3 A |

*Primary Examiner*—Henry R. Jiles
*Assistant Examiner*—Robert T. Bond
*Attorney, Agent, or Firm*—Connolly and Hutz

[57] ABSTRACT

A process for the purification of acid-containing crude caprolactam obtained by the rearrangement of cyclohexanone oxime, wherein the crude caprolactam is mixed with from 0.8 to 2.0 equivalents of a base, from 3 to 6 parts by weight of toluene, based on caprolactam and from 2 to 10 parts by weight of water, based on inorganic constituents, separating the mixture into a toluene phase and two aqueous phases the upper of which containing all contaminants and discarding this phase.

2 Claims, No Drawings

PURIFICATION OF CAPROLACTAM

This invention relates to a process for the purification of acid-containing crude caprolactam from the rearrangement of cyclohexanone oxime which is distinguished by the fact that the crude caprolactam is mixed with from 0.8 to 2.0 equivalents of a base—resulting in a pH-value of from 4 to 11—, from 3 to 6 parts by weight of toluene, based on caprolactam, and from 2 to 10 parts by weight of water, based on inorganic constituents, resulting in the formation in the aqueous phase of two layers of which the upper layer contains virtually all the impurities, and this layer is removed.

The rearrangement of cyclohexanone oxime to form caprolactem is known. The reaction is carried out either in the liquid phase with oleum as the rearrangement catalyst or in the gas phase in the presence of catalysts containing boric acid. The reaction mixture from the rearrangement with oleum generally contains from 1 to 2 moles of sulphuric acid per mole of caprolactam. On account of the volatility of the boric acid, the reaction product obtained in the gas phase generally contains from 0.5 to 5 mole % of boric acid.

German Auslegeschrift No. 1,031,308 describes a process for the purification of caprolactam obtained by rearrangement in oleum. From 1 to 10 parts by weight of benzene, based on the lactem, are added to the neutralised mixture obtained from the rearrangement reaction to extract the caprolactam, the caprolactam solution in benzene formed is separated from the aqueous phase, and caprolactam can be recovered therefrom by distillation. All the impurities remain in the aqueous phase, which has to be further processed.

This is obviated by the process according to the invention. A base, for example alkali metal hydroxide or ammonia, especially sodium hydroxide or potassium hydroxide, is added to the acid-containing crude caprolactam reaction mixture. The alkali metal hydroxides may be used either in solid form or in the form of an aqueous solution. Ammonia is generally used in the form of an aqueous solution. The base is used in such a quantity that a pH-value of from 4 to 11 is adjusted which takes from 0.8 to 2.0 equivalents of base, based on the acid in the crude caprolactam. From 3 to 6 parts by weight of toluene, based on the quantity of caprolactam, and from 2 to 10 parts by weight of water, based on the inorganic impurities, are added subsequently to or together with the base, the components are mixed and the mixture is left standing until the toluene phase and the aqueous phase separate. Two phases, namely a toluene phase and a water phase, are initially formed, the water phase consisting of two layers. Up to 50% by weight of the upper aqueous layer consists of impurities, the rest being water, lactam and traces of toluene. Although the formation of this layer is totally inexplicable, it is nevertheless a genuine third phase. This layer is liquid and may readily be separated off, for example by syphoning. If, therefore, the toluene phase is initially separated off and the aqueous phase is subsequently separated into its two layers, there are obtained a toluene phase, from which the pure caprolactam can be isolated by distillation or crystallization, an aqueous layer which contains the impurities and which may be destroyed or recycled, and an aqueous layer which contains sulphuric acid or boric acid, depending upon the initial process, and which may also be worked up by distillation or crystallization.

It is important to keep to the quantities of alkali, water and toluene quoted for carrying out the process because these quantities are critical.

In the following Examples, percentages are by weight.

EXAMPLE 1

1000 kg of filtered crude caprolactam, from the gas phase rearrangement of cyclohexanone oxime in the presence of a catalyst containing 6 g of boric acid, are pumped through a static mixer together with 4000 kg of toluene, 4 kg of NaOH and 50 kg of water (resulting in a pH of 10) and separated in a separation vessel.

4 kg of a liquid middle layer are formed.

This middle layer, which is separated off, consists of
1 kg of secondary products,
1.8 kg of water,
0.2 kg of caprolactam and traces of toluene and inorganic components.

The secondary products are very dark coloured, foul-smelling compounds, tar-like when dried. They are usually disposed of by burning.

Caprolactam of excellent purity is obtained from the organic phase, optionally after washing with water, by two step crystallization from toluene.

The lower aqueous layer is partially evaporated and sodium borate crystallizes from it in colourless crystals.

EXAMPLE 2

659 kg of a 30% by weight aqueous $NH_3$-solution, 691 kg of water and 1720 kg of toluene are added to and mixed with 1000 kg of the reaction product of cyclohexanone oxime and sulphuric acid, which contains approximately 570 kg of sulphuric acid and approximately 430 kg of caprolactam. The middle layer separated on standing (0.2 kg) is isolated. It contains
44% by weight of secondary products,
48% by weight of water,
4% by weight of lactam
2% by weight of toluene, and
2% by weight of ammonium sulphate.

Toluene and lactam are recovered from this middle layer by distillation. The top (toluene) layer and the bottom (aqueous) layer are processed as in example 1.

We claim:

1. A process for the purification of acid-containing crude caprolactam obtained by the rearrangement of cyclohexanone oxime, which comprises mixing the crude caprolactam with from 0.8 to 2.0 equivalents of a base, based on the acid in the crude caprolactam, so as to adjust the pH to from 4 to 11, from 3 to 6 parts by weight of toluene, based on the caprolactam, and from 2 10 parts by weight of water, based on the inorganic constituents, resulting in the formation of an organic phase and an aqueous phase having two layers; and removing the upper aqueous layer which contains substantially all the impurities.

2. A process as claimed in claim 1, wherein the base is an alkali metal hydroxide or ammonia.

* * * * *